(12) United States Patent
Skakoon

(10) Patent No.: US 9,332,968 B2
(45) Date of Patent: May 10, 2016

(54) SALIVA CONTAINER WITH OPTICAL VOLUME INDICATOR

(71) Applicant: Reflex Medical Corp., White Bear Lake, MN (US)

(72) Inventor: James G. Skakoon, St. Paul, MN (US)

(73) Assignee: Reflex Medical Corp., White Bear Lake, MN (US)

( * ) Notice: Subject to any disclaimer, the term of this patent is extended or adjusted under 35 U.S.C. 154(b) by 0 days.

(21) Appl. No.: 14/288,044

(22) Filed: May 27, 2014

(65) Prior Publication Data

US 2015/0064080 A1    Mar. 5, 2015

Related U.S. Application Data

(60) Provisional application No. 61/827,272, filed on May 24, 2013.

(51) Int. Cl.
  *B01L 3/00*    (2006.01)
  *A61B 10/00*    (2006.01)
  *H04W 4/00*    (2009.01)

(52) U.S. Cl.
  CPC ........... *A61B 10/0051* (2013.01); *B01L 3/5023* (2013.01); *H04W 4/001* (2013.01); *B01L 2300/0609* (2013.01)

(58) Field of Classification Search
  CPC .................................................. A61B 10/0051
  See application file for complete search history.

(56) References Cited

U.S. PATENT DOCUMENTS

| 1,883,971 A | 10/1932 | Kryzanowsky |
| 2,943,530 A | 7/1960 | Nagel et al. |
| 3,518,164 A | 6/1970 | Andelin et al. |
| 4,262,535 A * | 4/1981 | Andersson ...................... 73/428 |
| 4,283,498 A | 8/1981 | Schlesinger |
| 4,353,252 A | 10/1982 | Jeans |
| 4,580,577 A | 4/1986 | O'Brien et al. |
| 4,589,548 A | 5/1986 | Fay |
| 4,761,379 A | 8/1988 | Williams et al. |
| 4,768,238 A | 9/1988 | Kleinberg et al. |
| 4,932,081 A | 6/1990 | Burns |
| 5,260,031 A | 11/1993 | Seymour |
| 5,334,502 A | 8/1994 | Sangha |
| 5,997,121 A * | 12/1999 | Altfather et al. ................... 347/7 |
| 6,423,550 B1 | 7/2002 | Jenkins et al. |
| 2009/0216213 A1 | 8/2009 | Muir et al. |
| 2012/0046574 A1 * | 2/2012 | Skakoon ....................... 600/579 |

* cited by examiner

*Primary Examiner* — Paul Hyun
(74) *Attorney, Agent, or Firm* — Christensen Fonder P.A.

(57) ABSTRACT

A device with a vessel for saliva that has one or more optical indicators to show the volume of saliva in the container. The optical indicators use the principle of total internal reflection together with the difference in refractive index between saliva and air. In embodiments, suitable visual indicators are either visible or invisible, when reflecting surfaces are either not immersed or immersed in saliva or vice versa. The device may comprise a vessel with a saliva pathway, a saliva containment region defining a saliva reservoir, the reservoir having a desired fill level, and an optical viewing window adjacent an angled reflective surface for level indication and/or validating a fill level. The device may include patient interface components and chemical test strips.

18 Claims, 4 Drawing Sheets

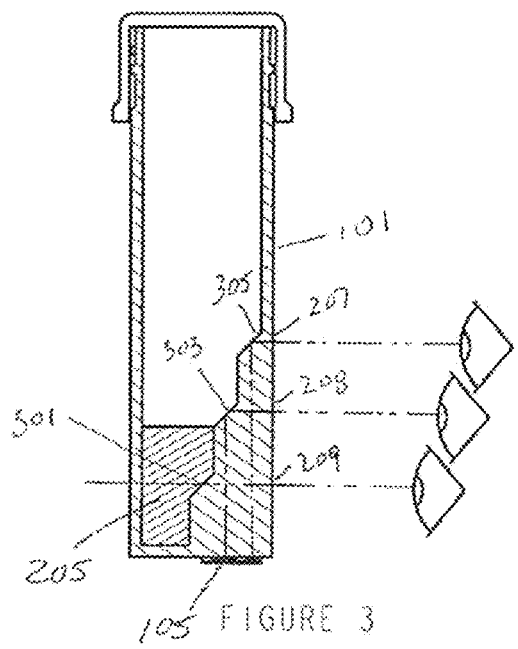
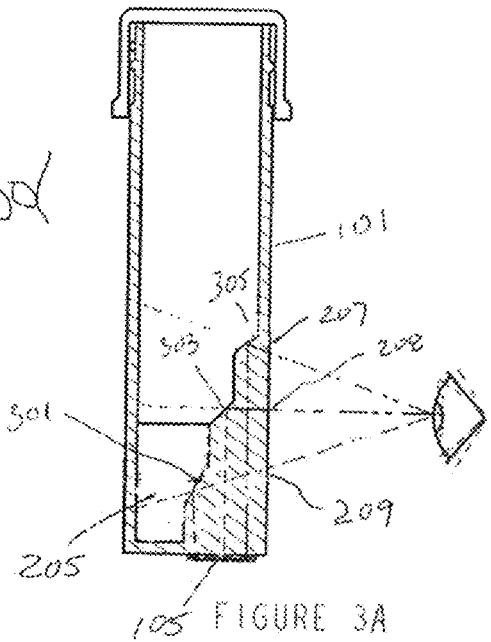
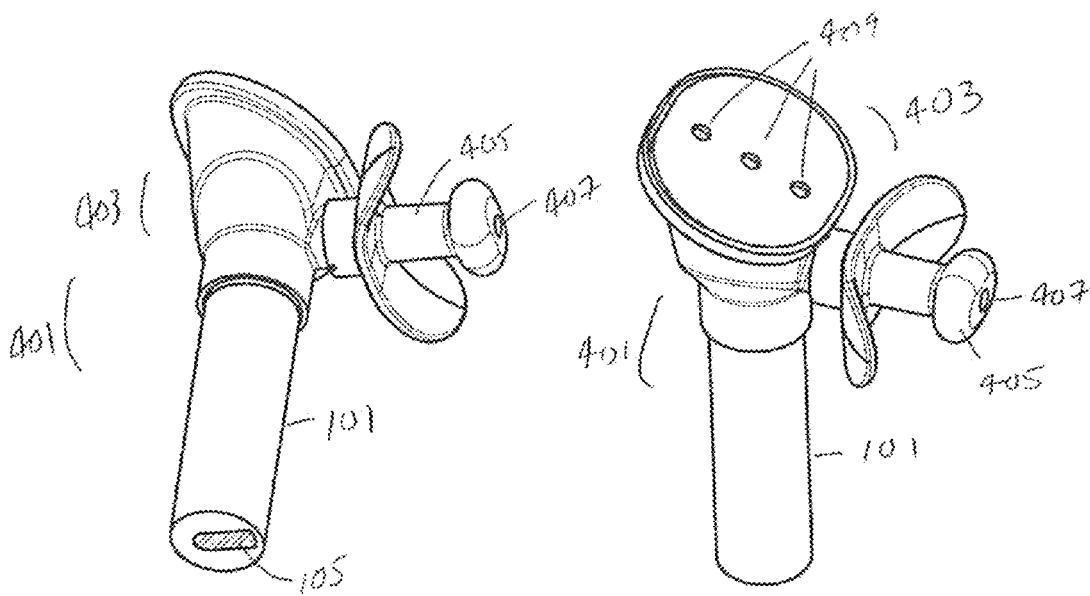
FIGURE 3  FIGURE 3A
FIGURE 4A  FIGURE 4B

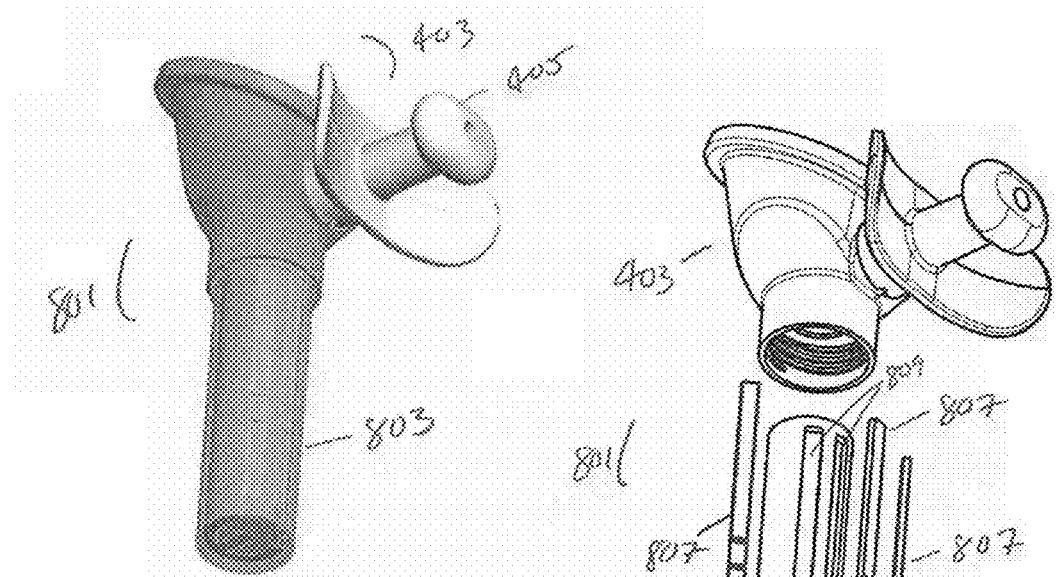
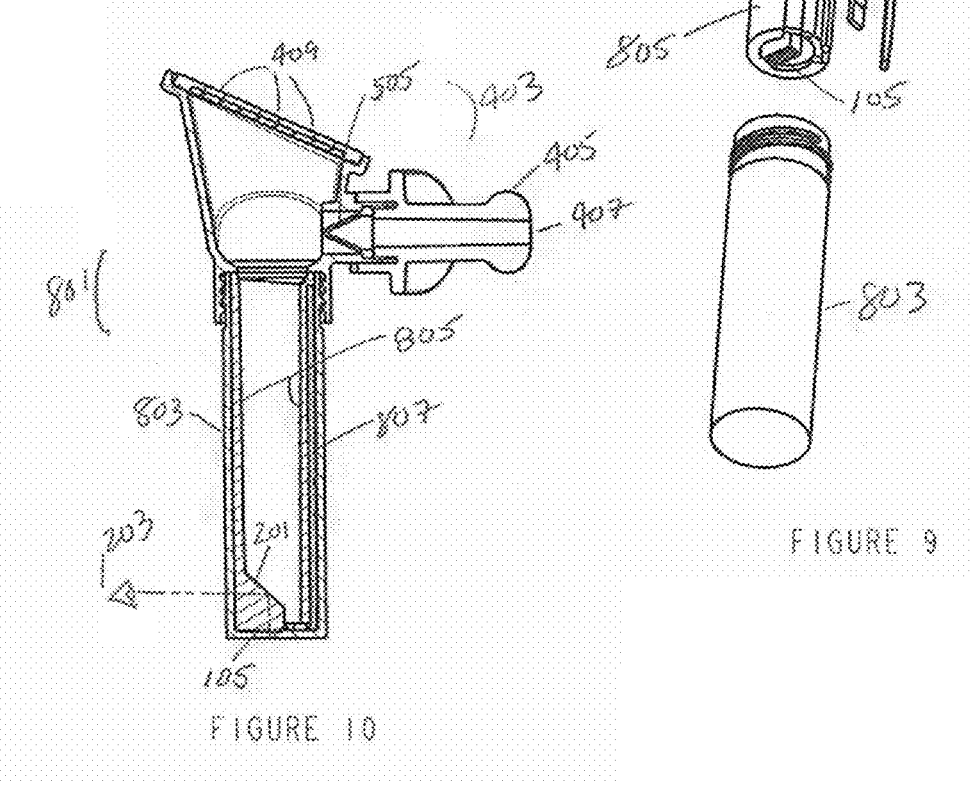

SALIVA CONTAINER WITH OPTICAL VOLUME INDICATOR

RELATED APPLICATION

The present application claims the benefit of U.S. Provisional Application No. 61/827,272, filed May 24, 2013, which is incorporated herein by reference in its entirety.

FIELD OF THE INVENTION

The present invention relates to devices for collecting saliva. In particular, the present invention relates to a saliva collection container with an optical indicator of the volume of saliva collected.

BACKGROUND OF THE INVENTION

Bodily fluids are collected for various reasons, including diagnosing illness, simple therapeutic removal, determining pregnancy, confirming or establishing levels of therapeutic agents, determining drug abuse, and profiling DNA composition. Blood, urine, and saliva are among the commonly collected bodily fluids for some or all of these purposes. Among these, saliva has an advantage over other fluids for ease of collection. This is especially true for drugs-of abuse-testing and for DNA testing.

Screening for drugs of abuse is performed by health professionals, law enforcement personnel, and government or private employers, among others. Substances of abuse that are commonly screened for include alcohol, cannabis, barbiturates, opiods, cocaine, amphetamines, and hallucinogens. For many such tests and testing environments, blood or urine collection is difficult, if not impossible, making saliva collection an appealing alternative. Saliva is less invasive to obtain than either blood or urine, and does not invoke privacy concerns to the same extent as does urine.

DNA testing is used for purposes of paternity, genealogy, disease susceptibility, and forensics, among others. Blood samples, buccal swabs, and saliva are commonly used for DNA tests. Collecting saliva is less invasive than collecting blood, and saliva collection can provide a larger, and therefore perhaps more reliable sample than buccal swabs.

Saliva samples are commonly collected by one of two methods: intra-oral sponge absorption and direct expectoration. An example of the first is U.S. Pat. No. 4,580,577 to O'Brien, et al., which discloses an absorbent mass that is masticated by the donor until saturated. The mass is placed in a squeezing device to expel saliva into a holding chamber, out of which a test aliquot can be removed. Sponge or sponge-like absorption methods are disclosed in numerous other patents, teaching variations such as added reagents, salivation promoters, preservatives, flavorings, chemical stabilizers, and a plurality of samples, among others.

A flaw of many saliva collection devices that use a sponge for collection is the inability to ascertain adequate sample size. Instructing a donor to "saturate" the sponge is ambiguous and not quantitative. Not only can this result in too little saliva for the intended subsequent use, but also in an unknown amount, even if above a minimum. For some uses such as, for example, chemical assay, a known volume is preferred over a "minimum" volume because the assay may require a relatively accurate volume. Just as important, collecting saliva is a relatively slow process. Unlike urine or blood, for example, saliva is not "cached" by the donor, and must be collected as it is produced. Therefore, it is extremely important not to collect more saliva than is required for subsequent use because this wastes time and adds stress to the persons involved in the collection process.

A volume adequacy indicator for use in sponge-type saliva collectors is disclosed in several prior art patents. U.S. Pat. No. 5,260,031 to Seymour, for example, discloses an integrated indicator that provides a visual cue that the sponge is adequately saturated. Another, similar device is disclosed in U.S. Pat. No. 6,423,550 to Jenkins, et al. Several commercially available devices include volume adequacy indicators that use dyes that either change color or are transported to a visually different place upon contact with saliva, which is read by the user as a volume adequacy indicator. One example of a commercially available device is the Quantisal™ device from Immunalysis, which corresponds to U.S. Pat. No. 5,260,031 to Seymour. Another example is the Oral-Eze® device from Quest Diagnostics®, which corresponds to U.S. Pat. No. 5,334,502 to Sangha.

The prior art volume indicators employed by sponge-type saliva collection devices require additional substituent components, including coloring dyes. These components add cost and, potentially, contaminate the collected specimen. Moreover, they often indicate only that a minimum volume has been collected, and not a specifically desired volume.

Just as important, sponge-based saliva collection itself has significant drawbacks. The sponge or sponge-like materials can adsorb saliva constituents, which may cause errors in subsequent analysis. The absorbent materials can cause discomfort for the donor, perhaps even precipitating a biological reaction. Placing and holding the sponge and sponge assembly into and in the mouth can be unpleasant for donors.

An example of a sample collection device based on direct expectoration is disclosed in U.S. Pat. No. 3,518,164 to Andelin, et al. This device includes a tube-like collector, an attached funnel, a stabilizing base, and a threaded sealing cap. The donor spits into the funnel, saliva collects in the tube, the funnel is removed, and the donated sample is sealed with the cap. In this invention, the collected volume is determined by reading the fluid meniscus against inscribed markings on the tube, similar to an ordinary graduated cylinder.

Other prior art example patents, which teach variations of direct saliva expectoration collection, and with sample volume indicators include:

U.S. Patent App. No. 20090216213 to Muir et al.
U.S. Pat. No. 4,283,498 to Schlesinger
U.S. Pat. No. 4,589,548 to Fay
U.S. Pat. No. 4,761,379 to Williams, et al.
U.S. Pat. No. 4,768,238 to Kleinberg, et al.
U.S. Pat. No. 4,932,081 to Burns All of these devices have inscribed markings on the container analogous to a graduated cylinder.

While container gradations are relatively common as volume indicators, and are usually accurate enough, reading them correctly can challenge device users. Proper technique requires that the fluid meniscus be discerned and aligned with the gradations, but discerning a fluid meniscus is not always simple, especially in challenging situations (low light, high stress, time-constrained). A consequence can be an erroneous volume reading, either too little or too much.

Therefore, there is a need for a saliva container that is a receptacle for neat saliva, and that has an unambiguous, easy-to-read indicator of saliva volume.

SUMMARY OF THE INVENTION

An embodiment of the present invention comprises a container for oral fluid (saliva) that employs one or more optical indicators to show the volume of saliva in the container. The optical indicators use the principle of total internal reflection together with the difference in refractive index between saliva and air. In embodiments, suitable visual indicators are either visible or invisible, when reflecting surfaces are either not immersed or immersed in saliva (or vice versa).

In embodiments, the device comprises a vessel with a saliva entry port, a saliva conduit defining a saliva pathway, a saliva containment region defining a saliva reservoir, the reservoir having a desired fill level, and an optical viewing window adjacent an angled reflective surface in the interior, and visual markings positioned to be reflected off the angled reflective surface for level indication and/or validating a fill level. Embodiments are useful as sub-components of known saliva collection devices and point-of-collection drugs-of-abuse test devices.

A feature and advantage of embodiments of the invention is that certainty is provided in whether or not there is an adequate amount of sample.

A feature and advantage of embodiments of the invention is that enhanced visual verification of the adequacy of the volume of saliva in the device is provided utilizing conventional materials and can be provided exclusively or partially by the molded configuration of the vessel.

A feature and advantage of embodiments is that a plurality or multiple reflective surfaces at different fill levels may be provided.

A feature and advantage is that the properties of the polymer forming the molded container are utilized to provide the visual indicator.

A feature and advantage of embodiments is that several levels of fill may be identifiable, provide information such as how much more saliva is needed if the current level is not adequate,

BRIEF DESCRIPTION OF THE FIGURES

The invention can be understood in consideration of the following detailed description of various embodiments of the invention in connection with the accompanying drawings, in which:

FIG. 1A is a cross-sectional view taken at line I-I of FIG. 2B;

FIG. 1B is a cross-sectional view taken at line I-I of FIG. 2B;

FIG. 1C is a cross-sectional view taken at line I-I of FIG. 2B;

FIG. 1D is a further embodiment of a cross sectional view taken at line I-I of FIG. 2B;

FIG. 1E is a view of a window of a vessel in accord with the invention with an image of an "insufficient saliva" marking.

FIG. 1F is a view of a window of a vessel in accord with the invention with an image of a "sufficient saliva" marking.

FIG. 3 is an orthogonal cross-section view showing an alternate embodiment of the present invention showing a plurality of optical volume indicators;

FIG. 3A is an orthogonal cross-section view showing an alternate embodiment of the present invention showing a plurality of optical volume indicators;

FIGS. 4A and 4B are perspective views of a saliva collection device, according to an embodiment of the invention;

FIG. 8 is a perspective view of a point-of-collection drugs-of-abuse test device, according to an embodiment of the invention;

FIG. 9 is an exploded perspective view of the device in FIG. 8; and

FIG. 10 is an orthogonal cross-section view of the device of FIGS. 8 and 9.

DETAILED DESCRIPTION

Figure 1:
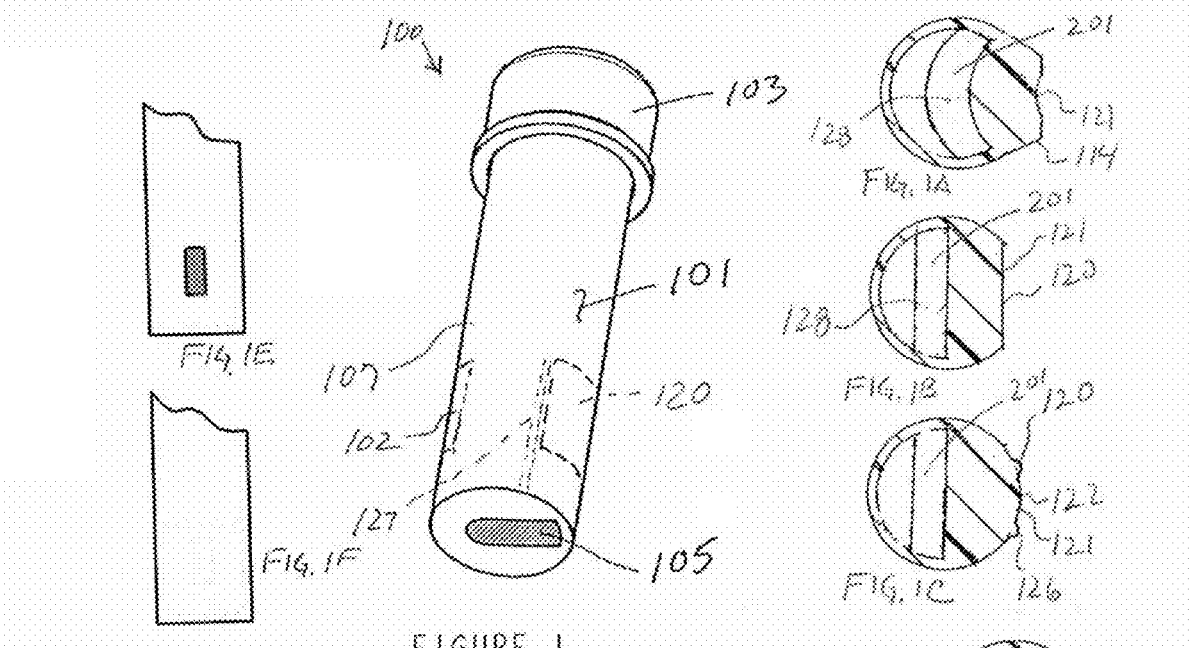
FIG. 1 is a perspective view of saliva container assembly, according to an embodiment of the invention.
Figures 2A, 2B:
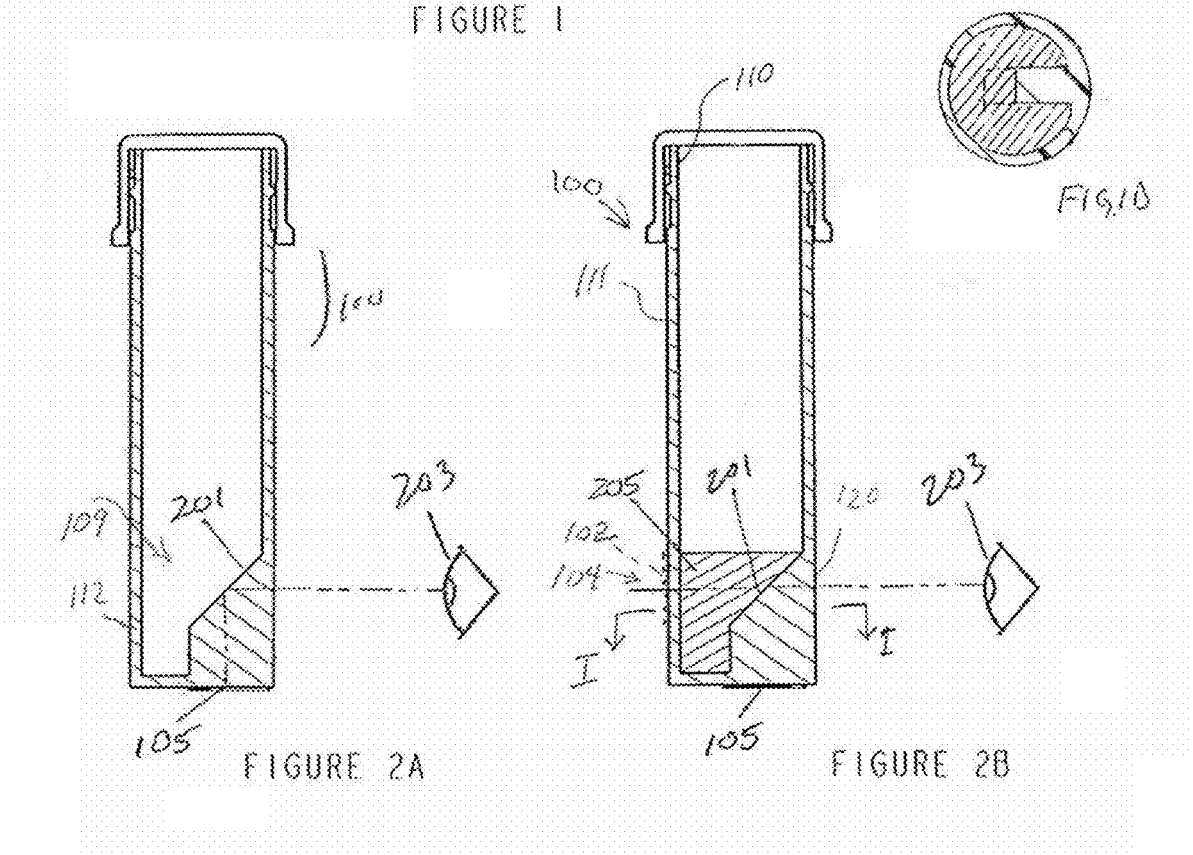
FIG. 2A is an orthogonal cross section view of the saliva container assembly of FIG. 1, showing the optical volume indicator without saliva.
FIG. 2B is the same view as FIG. 2A, but with the optical volume indicator immersed in saliva.

Referring now to FIGS. 1-1C, there is shown a saliva container 100 that includes a collection vessel 101 and a cap 103, which is releasably attached to saliva vessel 101. Collection vessel 101 may be made from a suitable optically clear material, such as, for example, polypropylene, polystyrene, poly methyl methacrylate, or glass. In embodiments, portions may be formed of the optically clear material and other portions opaque or translucent. Such separate portions may be joined by welding or overmolding, for example. Saliva container 100 includes a visual marking 105. Visual marking 105 can be a letter or other indicia, figure, or, as illustrated in FIG. 1, a simple printed or dyed color splotch applied to collection vessel 101. Additional marking 102 may be applied to the region 104 where the light will be transmitted from when the saliva is to a level that covers the reflective surface such as is illustrated in FIG. 2B. The vessel may be generally cylindrical shaped with respect to the exterior surface 107, and have interior structure 109, including the reflective surface 201, formed during molding such that said interior structure is unitary with the rest of the vessel. Vessel structure includes a mouth 110, a conduit region 111, and a saliva reservoir region 112. Exterior surface structure 114 may additionally include defined viewing structure 120, including exterior optical structure 121 which may have alternative configurations, including but not limited by, those illustrated by the cross sections of FIGS. 1A-1C. Such structure can guide the user to the correct viewing window 122 and can provide enhanced optics such as focused, enhanced, magnified, and/or widened image, as well as ribs 126 or other indicia or structure 127 to define or identify the location of the window. Such exterior structure can extend to the bottom of the container for molding simplicity. The interior optical structure 128 can complement the exterior optical structure 121 to create the desired enhanced imaging such as shown in particular in FIG. 1A. The vessel can have an internal diameter of about 0.4 to 0.6 inches in an embodiment with a saliva reservoir sized for about 1.0 ml. "Sized" meaning the positioning of the optical structure and markings positioned to indicate when the saliva is at least 1.0 ml. In other embodiments, the structure and markings are positions to indicate a saliva fill level of 0.8 to 1.2 ml. In other embodiments, the structure and markings are positions to indicate a saliva fill level of 0.5 to 1.5 ml.

In embodiments the saliva conduit can define a saliva flow path with a cross sectional area of 0.10 inches square to 0.30 inches square and a reservoir cross sectional area that changes depending on the level and whereby changes are associated with reflective surfaces. In embodiments the reservoir may be cylindrical with an inside diameter of 0.4 to 0.7 inches. In embodiments the reservoir may be cylindrical with an inside diameter of 0.6 to 0.9 inches. In embodiments the reservoir may be cylindrical with an inside diameter of 0.4 to 0.7 inches. In embodiments the reservoir may be cylindrical with an inside diameter at an upper portion thereof of 0.3 to 0.8 inches. In embodiments, the reservoir has steps associated with different indicating levels.

FIGS. 2A and 2B show reflective surface 201, which is a functional element of the optical volume indicating feature of the claimed invention. The functioning of the optical volume indicator is as follows: Observer 203 looks toward reflective surface 201 in the spatial configuration shown. In the absence of saliva, reflective surface 201 is a solid/gas interface and, due to the principle of total internal reflection, will reflect the visual marking 105 to observer 203. However, if a liquid such as saliva 205 covers reflective surface 201 (FIG. 2B), the respective refractive index combination of the two interface materials no longer exhibits total internal reflection, and visual marking 105 is no longer reflected to observer 203.

The principle of total internal reflection is a well-known optical phenomenon whose basis is the difference in the speed of light in various transmission media. This difference causes light beams to change direction, or refract, at the interface of two different media. However, if the angle of incidence of light to the interface is beyond a critical angle, governed by the indices of refraction for the two media, all light is reflected rather than refracted. Because of the different refractive indices of the materials involved (e.g. clear plastic, saliva, and air), the critical angle is different enough between the two conditions, saliva and air, to make the necessary geometry convenient to construct. This general principle has been employed in numerous prior art liquid level sensing devices and is described in suitable detail throughout the patent literature. Examples include U.S. Pat. No. 1,883,971 to Kryzanowsky, U.S. Pat. No. 2,943,530 to Nagel, and U.S. Pat. No. 4,353,252 to Jeans. Said patents are incorporated herein by reference.

FIGS. 1E and 1F illustrate a visual indication a user might see of an insufficient quantity of saliva, such as provided by an empty container of FIG. 2A and an adequate supply of saliva as illustrated in FIG. 2B.

FIG. 3 shows an additional embodiment of the claimed invention in which a plurality of reflective surfaces (reflective surface A 301, reflective surface B 303, and reflective surface C 305) of saliva container 100 are depicted. In this embodiment, observer 203 can discern multiple saliva volume levels through three viewing windows or regions 207, 208, 209.

FIG. 3A illustrates an arrangement where the optical surfaces may be configured such that the vessel does not have to be repositioned for viewing the separate reflective surfaces in that the reflective angles are different to converge the respective indicating images. Although not illustrated, exterior optical structure may be modified as well to provide this feature.

The claimed invention can be used in conjunction with, or as part of any type of saliva collection device, although it is best suited to the spongeless types. One suitable saliva collector example that uses the present invention is the saliva collection device 401, shown in FIG. 4. Collection vessel 101 has been relieved of cap 103, which has been replaced with header assembly 403. Header assembly 403 includes a mouthpiece 405, which includes a saliva inlet 407. Header assembly 403 also includes a vent 409 (or vents). An embodiment of a header assembly 403 is also described in US Patent Application No. 20120046574, which is herein incorporated by reference in its entirety.

Figure 5:
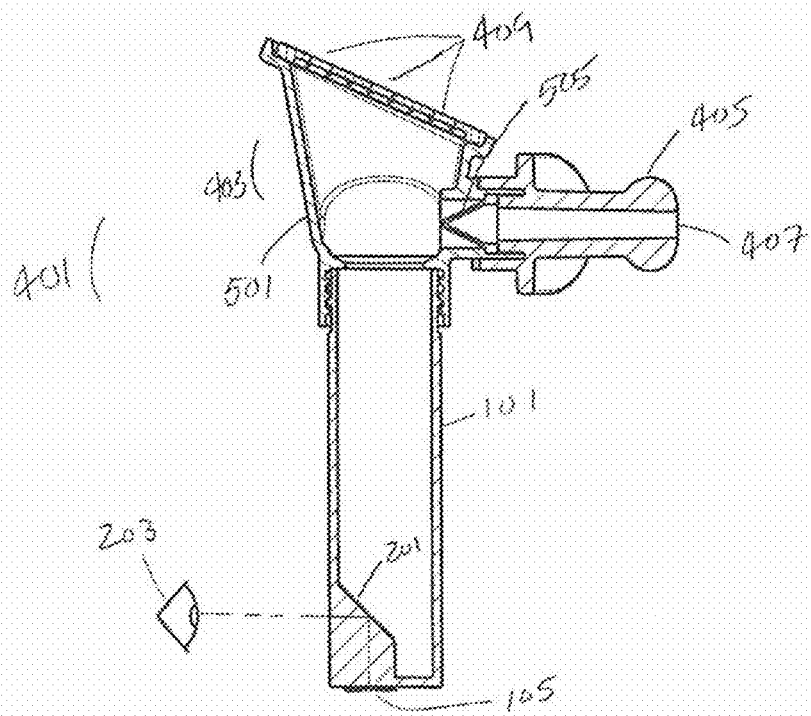
FIG. 5 is an orthogonal cross-section view of the saliva collection device of FIGS. 4A and 4B.

FIG. 5 shows the internal components of saliva collection device 401, including a header housing 501 attached to the aforementioned mouthpiece 405, and a valve 505, which is in fluid communication with the saliva inlet 407, and a vent 409 integrated into an outer wall of header housing 501. Vent 409 can be covered by a vent membrane (not shown), which prevents escape of saliva through the vent, yet permits escape of air during saliva donation. Collection vessel 101 is removably attached to header housing 501.

To use the saliva collection device 401, a saliva donor places mouthpiece 405 into the mouth and spits and blows. Saliva enters saliva inlet 407, flows through valve 505, and into header housing 501. Air expelled by the donor is vented out of saliva collection device 401 through vent 409, whereas saliva flows downward into collection vessel 101. Observer 203, who can also be the donor, watches for the expected optical effect to determine when the desired saliva volume has accumulated. This corresponds to a volume that just covers reflective surface 201, which makes visual marking 105 invisible to observer 203. So if, for example, visual marking 105 is a blue stripe or patch, observer 203 will initially see a corresponding blue patch reflection when looking straight on as shown in FIG. 4. This blue reflection disappears once the predetermined saliva volume is accumulated, and observer 203 will know to stop the donation. After the donation is complete, header assembly 403 can be removed, and a seal such as cap 103 can be reapplied so that the saliva sample can be stored or transported for subsequent use.

Figure 6:
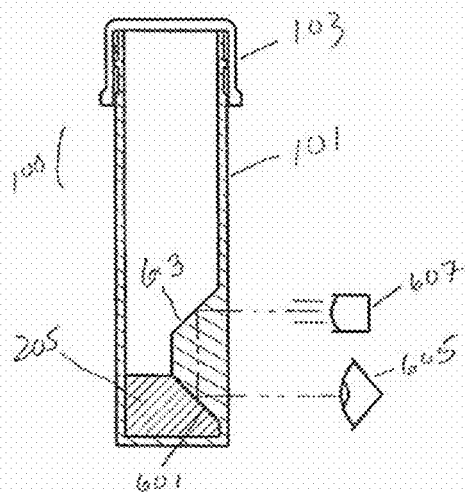
FIG. 6 is an orthogonal cross-section view showing an alternate arrangement for the optical volume indicator of the invention.

The alternate embodiment of the present invention shown in FIG. 6 uses two reflecting surfaces disposed within collection vessel 101. Reflective surface A 601 serves as the volume indicating surface, whereas reflective surface B 603 allows a different pathway for incident light. This arrangement, is particularly-well suited for electronically reading the optical volume indicator. So, for example, rather than the human eye being observer 203, a photosensor 605 can be the observer, and a light emitting diode 607 can replace the visual marking 105. Moreover, because the signal strength can be calibrated to a corresponding percentage of immersion of reflective surface A 601, it is also possible using this scheme to discern a percentage of a fill volume as well.

Figure 7:
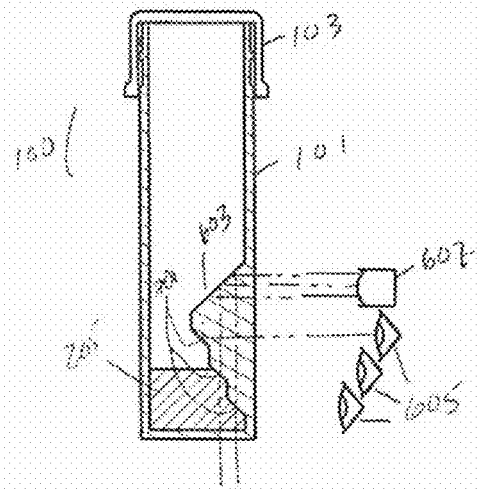
FIG. 7 is an orthogonal cross-section view showing a plurality of optical volume indicators configured like the alternate arrangement of FIG. 6.

This principle can be extended to a plurality of optical indicators by disposing a bank of discrete optically reflective surfaces within collection vessel 101 as shown in FIG. 7. In this example, a single light source, light emitting diode 607, is used to illuminate three reflective surfaces 701 by being reflected by reflective surface B 603. As each surface is immersed in saliva, the corresponding electronic signal changes state.

A common use for collected saliva is in drugs-of-abuse screening tests. These tests often use lateral flow immunoassay reagent strips to test for the presence of drugs of abuse such as barbiturates, opioids, methamphetamine, THC, and so on. By using lateral flow immunoassay strips, an immediate, albeit preliminary, result can be obtained at the point-of-collection, avoiding the need to transport the screening sample to a laboratory.

The present invention can be incorporated into a saliva collection device that also includes lateral flow immunoassay strips. One such device embodiment is shown in FIG. 8. A saliva collection and screening device 801 includes a mouthpiece 405, a header assembly 403, and a collection vessel 803, and also includes the herein described optical volume indicator.

Referring now to FIG. 9, header assembly 403 is analogous to the already-described header assembly 403 shown in FIGS. 4 and 5, and accepts collection vessel 803. An insert 805 is positioned within collection vessel 803, and a plurality of immunoassay strips 807 is disposed into slots 809 of insert 805. Insert 805 includes reflective surface 201 (shown in FIG.

10), as well as visual marking 105, which in this case is a color splotch. A possible alternate embodiment places visual marking 105 on either the inside or outside bottom of collection vessel 803. Other visual markings may be on the side of the vessel.

The function of screening device 801 is described, with reference to FIG. 10, as follows. A donor spits and blows saliva into mouthpiece 405 as before. Air flows out vent 409, and saliva flows downward into collection vessel 803 as before. Insert 805 is, in this embodiment, a hollow cylinder that directs the saliva to the bottom of collection vessel 803, and also isolates immunoassay strips 807 from the downward flowing saliva. Once the saliva reaches the bottom (saliva 205 not shown), it can be taken up by the bottom ends of immunoassay strips 807, which is the prescribed test method for these immunoassay strip elements. The saliva donation continues until observer 203, which in this case could be a drug-test administrator, sees the optical volume indicator change state as previously described. This confirms that an adequate volume of saliva has been collected to run the immunoassay strip tests to completion, regardless of the test progress. Saliva donation can then be terminated, yet still letting the tests run to completion. This embodiment offers a clear advantage for oral drugs-of-abuse testing wherein the needed collected volume is minimized, thus speeding and simplifying the test methodology.

The embodiments above are intended to be illustrative and not limiting. Additional embodiments are within the claims. In addition, although aspects of the present invention have been described with reference to particular embodiments, those skilled in the art will recognize that changes can be made in form and detail without departing from the spirit and scope of the invention, as defined by the claims.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

The above references in all sections of this application are herein incorporated by references in their entirety for all purposes.

All of the features disclosed in this specification (including the references incorporated by reference, including any accompanying claims, abstract and drawings), and/or all of the steps of any method or process so disclosed, may be combined in any combination, except combinations where at least some of such features and/or steps are mutually exclusive.

Each feature disclosed in this specification (including references incorporated by reference, any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment (s). The invention extends to any novel one, or any novel combination, of the features disclosed in this specification (including any incorporated by reference references, any accompanying claims, abstract and drawings), or to any novel one, or any novel combination, of the steps of any method or process so disclosed The above references in all sections of this application are herein incorporated by references in their entirety for all purposes.

Although specific examples have been illustrated and described herein, it will be appreciated by those of ordinary skill in the art that any arrangement calculated to achieve the same purpose could be substituted for the specific examples shown. This application is intended to cover adaptations or variations of the present subject matter. Therefore, it is intended that the invention be defined by the attached claims and their legal equivalents, as well as the following illustrative aspects. The above described aspects embodiments of the invention are merely descriptive of its principles and are not to be considered limiting. Further modifications of the invention herein disclosed will occur to those skilled in the respective arts and all such modifications are deemed to be within the scope of the invention.

For purposes of interpreting the claims for the present invention, it is expressly intended that the provisions of Section 112, sixth paragraph of 35 U.S.C. are not to be invoked unless the specific terms "means for" or "step for" are recited in a claim.

What is claimed is:

1. A container for collecting saliva comprising:
a collection vessel with a saliva reservoir;
a cap for the collection vessel;
the collection vessel including a reflecting surface in or at the saliva reservoir providing a changeable reflecting characteristic dependent of the presence of saliva at the reflecting surface;
a visual marker, secured to the collection vessel, that is one of viewable or not viewable by an observer when looking from a side of the collection vessel at the reflecting surface dependent upon the changeable reflecting characteristic;
wherein the visual marker is disposed at a bottom end of the collection vessel opposite the cap; further wherein the visual marker is reflected to the observer, due to total internal reflection, when no saliva is present at the reflecting surface; further wherein the visual marker is not reflected to the observer when a sufficient volume of saliva is present in the saliva reservoir to be disposed at the reflecting surface;
the container further having gradations indicating collected volume.

2. The container of claim 1 wherein the visual marker comprises a colored area.

3. The container of claim 1 comprising a plurality of reflecting surfaces.

4. The container of claim 1 wherein the visual marker is disposed below the reflecting surface.

5. The container of claim 1 wherein the visual marker comprises one of a figure and text.

6. A container for collecting saliva comprising:
a collection vessel with a saliva reservoir;
a cap for the collection vessel;

the collection vessel including a reflecting surface in or at the saliva reservoir providing a changeable reflecting characteristic dependent of the presence of saliva at the reflecting surface;

a visual marker, secured to the collection vessel, that is one of viewable or not viewable by an observer when looking from a side of the collection vessel at the reflecting surface dependent upon the changeable reflecting characteristic;

wherein, due to total internal reflection, the visual marker is visible when said collection vessel is empty, and invisible when said collection vessel is filled with a predetermined volume of saliva;

wherein the visual marker is disposed at a bottom end of the collection vessel opposite the cap; further wherein the visual marker is reflected to the observer, due to total internal reflection, when no saliva is present at the reflecting surface; further wherein the visual marker is not reflected to the observer when a sufficient volume of saliva is present in the saliva reservoir to be disposed at the reflecting surface;

the container in combination with electronic sensors for determining whether the visual marker is visible or invisible.

7. A device for collecting saliva comprising:
a mouthpiece coupled to a housing, the mouthpiece including an inlet;
a collection vessel attached to said housing;
the collection vessel including a viewing window disposed at a side of the collection vessel, a reflecting surface, and a visual marker secured to the collection vessel below the reflecting surface or opposite the viewing window;
wherein, due to total internal reflection, the visual marker is one of visible and invisible when the collection vessel is viewed through the viewing window when said collection vessel is empty, and the other of visible and invisible when the collection vessel is viewed through the viewing window and when the collection vessel is filled with a predetermined volume of saliva;
further wherein the visual marker is a colored area disposed at an end of the collection vessel opposite the housing.

8. The device of claim 7 wherein said housing includes an outlet vent.

9. The device of claim 7 wherein the collection vessel is one of partially and fully transparent.

10. The saliva collection device of claim 7 comprising a plurality of discrete optical structures each located at different levels inside the vessel and each associated with a saliva fill level.

11. The device of claim 7 further comprising an electronic sensor for determining one of visible and invisible.

12. The device of claim 7 further comprising a plurality of chemical test strips positioned in an insert disposed in the collection vessel.

13. The device of claim 7, wherein the colored area is disposed on a side of the reflecting surface opposite the mouthpiece; further wherein the colored area is visible when the collection vessel is viewed through the viewing window when the collection vessel is empty and the colored area is invisible when the collection vessel is viewed through the viewing window when the collection vessel is filled with a predetermined volume of saliva.

14. A device for collecting saliva comprising:
a mouthpiece coupled to a housing, the mouthpiece including an inlet;
a collection vessel attached to said housing;
an insert disposed within said collection vessel, said insert including a plurality of slots;
a plurality of immunoassay test strips positioned within said slots;
at least one of said insert and said collection vessel including a reflecting surface, a viewing window, and a visual marker;
wherein, due to total internal reflection at the reflecting surface, the visual marker is one of visible and invisible when viewed through the viewing window when said collection vessel is empty, and the other of visible and invisible when viewed through the viewing window when said collection vessel is filled with a predetermined volume of saliva, and wherein said predetermined volume of saliva is adequate for said plurality of immunoassay test strips.

15. The device of claim 14 wherein the test strips comprise lateral flow immunoassay strips and wherein the lateral flow immunoassay strips determine the presence of one or more of barbiturates, THC, opioids, amphetamines, cocaine, and PCP.

16. The device of claim 14 further having an outlet and wherein said outlet vent is covered by a liquid retaining membrane.

17. The saliva collection device of claim 14 comprising a plurality of discrete optical structures each located at different levels inside the vessel and each associated with a saliva fill level.

18. A device for collecting saliva comprising:
a mouthpiece coupled to a housing, the mouthpiece including an inlet;
a collection vessel attached to said housing;
the collection vessel including a viewing window disposed at a side of the collection vessel, a reflecting surface, and a visual marker secured to the collection vessel below the reflecting surface or opposite the viewing window;
wherein, due to total internal reflection, the visual marker is one of visible and invisible when the collection vessel is viewed through the viewing window when said collection vessel is empty, and the other of visible and invisible when the collection vessel is viewed through the viewing window and when the collection vessel is filled with a predetermined volume of saliva; and
an electronic sensor for determining whether the visual marker is visible or invisible.

* * * * *